United States Patent [19]

Bonaldo

[11] Patent Number: 4,950,260

[45] Date of Patent: Aug. 21, 1990

[54] MEDICAL CONNECTOR

[75] Inventor: Jean M. Bonaldo, Upland, Calif.

[73] Assignee: SafetyJect, Costa Mesa, Calif.

[21] Appl. No.: 431,850

[22] Filed: Nov. 2, 1989

[51] Int. Cl.⁵ .............................................. A61M 25/00
[52] U.S. Cl. ..................................... 604/283; 604/905
[58] Field of Search ............... 604/283, 280, 263, 256, 604/905

[56] References Cited

U.S. PATENT DOCUMENTS 4,022,205  5/1977  Tenczar ........................... 604/905 X
4,349,024  9/1982  Ralston, Jr. ..................... 604/905 X
4,752,292  6/1988  Lopez et al. ..................... 604/283 X Primary Examiner—John D. Yasko
Attorney, Agent, or Firm—Robert R. Thornton

[57] ABSTRACT

A connector for use in introducing medication into a patient having a pair of plastic tubular members adapted to be manually pushed together to engage in a mating relationship with a locking mechanism that selectively secures the members together. One of the members has a sealed entry port at its end and the other member contains a needle which centrally pierces the seal of the port upon engagement of the members.

3 Claims, 2 Drawing Sheets

MEDICAL CONNECTOR

BACKGROUND OF THE INVENTION

This invention relates to medical connectors of a type utilized for introducing medication into a patient, typically through intravenous injection.

Devices of this type are well known in the art. One such device, for example, is described in U.S. Pat. No. 4,752,292 issued June 21, 1988. While such devices have found widespread acceptance in the medical field as particularly adapted to avoid the possibility of accidental contamination of medical personnel with fluids by reason of accidental sticking of the personnel by needles contained in the devices, such devices as have been widely used heretofore have been comparatively expensive by reason of their construction features. For example, such devices typically are molded from medical grade plastics and involve relatively expensive molds as well as assembly procedures. These devices are typically intended for disposal after usage on a given patient.

SUMMARY

A medical connector according to the present invention includes a male port element having a longitudinal passage terminating at one end in sealing means which is of the self-sealing type and a housing element having a longitudinal cavity therein open at one end thereof adapted to receive said port element, a hollow needle disposed within the cavity so that the needle tip penetrates the sealing means upon insertion of the port element into the cavity; and means for detachably locking the housing element and the port element together when said port element is inserted into the cavity including a locking cap element flexibly attached to the housing open end and operable to seal the housing open end and a locking recess formed on the port element and operable to receive the cap element when inserted thereinto to lock the port element and the housing element together in a mating relationship.

BRIEF DESCRIPTION OF THE DRAWING

The invention may be more readily understood by referring to the accompanying drawing, in which.

DETAILED DESCRIPTION OF THE PREFERRED EMBODIMENT

Figure 1:
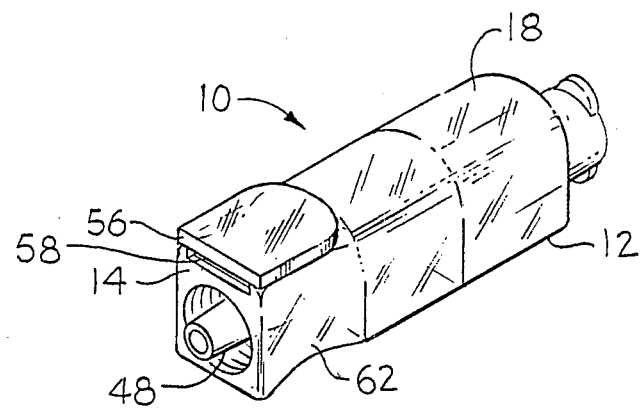
FIG. 1 is an isometric view of a medical connector according to the present invention.
Figure 2:
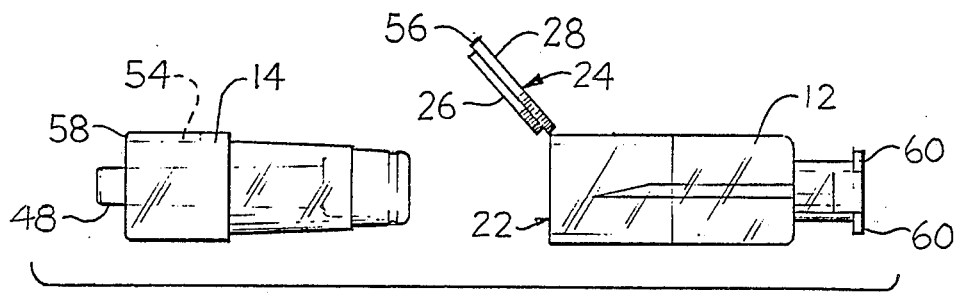
FIG. 2 is a side elevation of the medical connector of FIG. 1 showing the housing element and the injection port element in their separated disposition.
Figure 3:
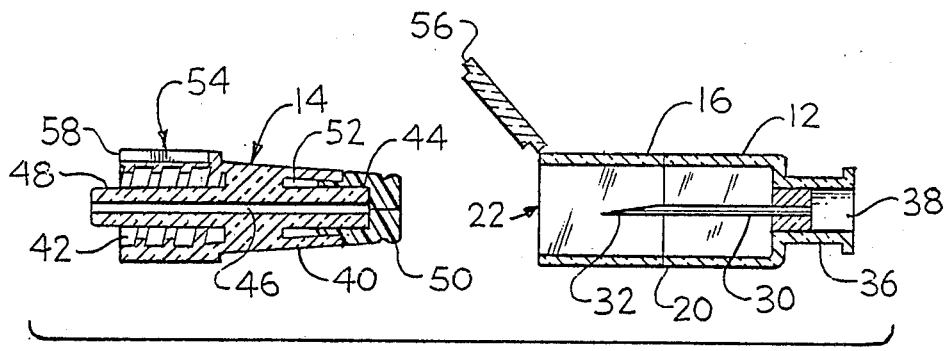
FIG. 3 is a view, in section, of the housing element and injection port element as shown in FIG. 2.

Referring now to FIG. 1, there is shown a medical connector pin according to the present invention which consists of a housing element portion 12 and an injection port element portion 14 connected together in their mating relationship. FIG. 2 is a side elevational view of the housing element portion 12 and injection port element 14 separated from their mating relationship. FIG. 3 is a side elevational view, in section, of the housing element portion 12 and injection port element portion 14 in the disposition shown in FIG. 2, to better illustrate the internal structure thereof.

Figure 4:
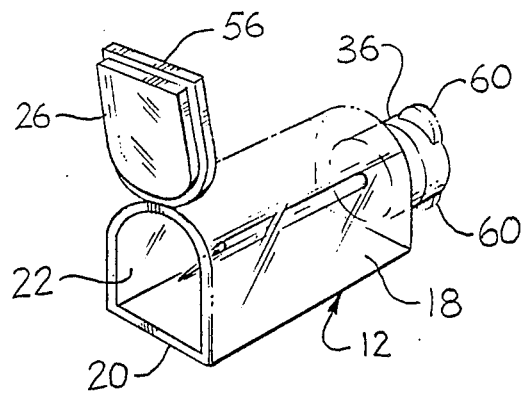
FIG. 4 is an isometric view of the housing element in its open disposition.

As is best seen in FIGS. 2 and 3, the housing element portion 12 which typically is made of any of a number of medical grade transparent plastic materials, has a barrel portion 16 which is hollow with a curvilinear top and side portion 18, best shown in FIG. 4, and a generally flat base portion 20. The flat base portion is preferred as facilitating the positioning of the connector 10 on the body surface of the patient as contrasted to a cylindrical base for stability purposes. The barrel portion 16 has an open end 22 at one end thereof. Adjacent the end 22 a cap 24 is flexibly connected to the barrel portion by being integrally molded thereto in the preferred embodiment. The cap 24 has a seal portion 26 which is complementary in size and cross-sectional configuration to the open end 22 of the barrel portion 16. The cap has an overlying flap portion 28 which extends beyond the periphery of the sealed portion and, in the preferred embodiment, is coincident with the outer surface configuration of the barrel portion 16.

A hollow needle 30 having a pointed end 32 is disposed within the hollow barrel portion 16 and terminates opposite the pointed needle end within a plug 34 formed within a constricted inlet portion 36 of the housing element portion 12 formed integrally with the barrel portion 16 opposite the open end 22. The constricted inlet portion 36 has a hollow central portion 38 for receiving fluid flow tubing or the like to supply fluid to the needle 30.

The injection port element portion 14 has a frustoconically tapered portion 40 which terminates at one end in a threaded annular recess 42 remote from the small end of the frustoconical taper and, at the opposite end thereof, in a blunt small end 44 a fluid passage 46 extends axially through the injection port element 14. A boss 48 is formed on the injection port element 14 at the annular recess 42 to provide one end of the termination of the fluid passage 46. At the opposite end of the fluid passage 46, a seal 50 of the resealable type, which may be constructed of any of a number of conventional materials such as latex, closes the opposite end of the fluid passage 46. The seal 50 is positioned in an annular recess 52 formed at the blunt small end 44 of the frustoconical tapered end 40 so as to be held in place.

Figure 5:
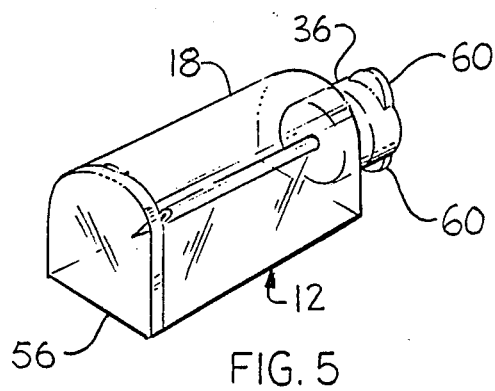
FIG. 5 is an isometric view of the housing element in its closed disposition.
Figure 6:
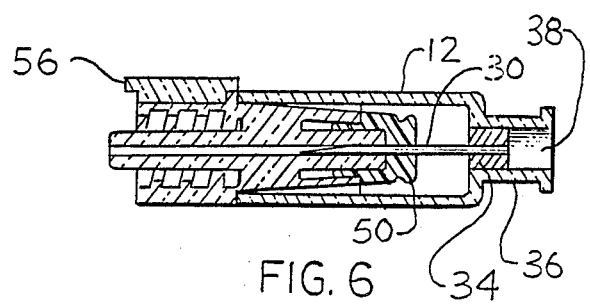
FIG. 6 is a side elevational view, in section, of the medical connector shown in FIG. 1.
Figure 7:
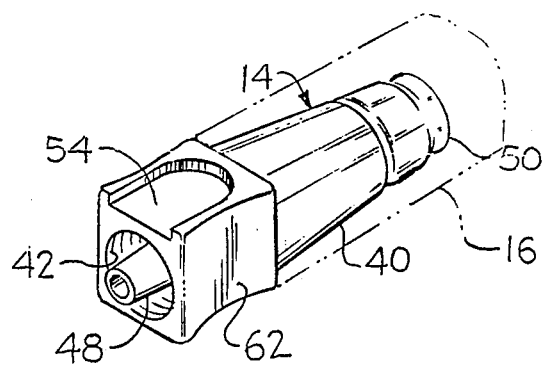
FIG. 7 is an isometric view of the injection port element separated from the housing element.
Figure 8:
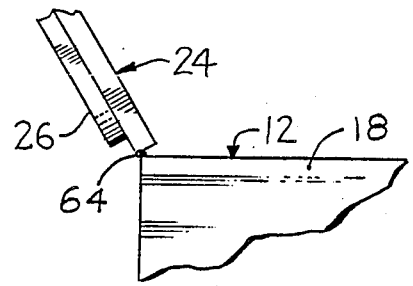
FIG. 8 is a partial electronical view of the housing element illustrating the hinged connection of the cap to the housing element.

In operation, the frustoconically tapered portion 40 of the injection port 14 is inserted into the open end 22 of the housing element barrel portion 16, causing the needle point 32 to pierce the seal 50 and extend into the longitudinal passage 46, thereby providing fluid communication through the medical connector 10 when so disposed in such a mating relationship as is shown in FIG. 7. In order to hold the medical connector housing element 12 and injection port element 14 in this mating relationship, the injection port element 14 has a locking recess 54 formed therein adjacent the cap 24. The locking recess 54 is complementary in size and cross-sectional configuration to the sealed portion 26 of the cap 24 and is disposed with respect thereto so that, when the medical connector is assembled as is shown in FIG. 7, the cap can be manually depressed to press fit the sealed portion 26 into the locking recess 54. When it is desired to separate the housing element 12 from the injection port element 14, the cap 24 may be manually removed from the locking recess 54 by outward pressure on a lift tab portion 56 at the edge of the flap portion 28 of the cap 24. The lift tab portion 56 may be manually accessed by inserting a fingernail, for example, in the open end 58 of the locking recess 54 underlying the lift tab 56. The housing element 12 can then be separated from the injection port element 14 and the pointed needle end 32 sealed against accidental sticking of medical personnel handling the housing element 12 by closing the barrel element open end 22 with the seal portion 26 of the cap 24, which also forms a press fit seal therewith. As is seen in FIG. 5, when so sealed, the cap 24 forms a flush closure of the housing element open end 22, so as to avoid accidental opening thereof.

In order to facilitate the mating and separation of the housing element 12 and injection port element 14, the housing element 12 has a pair of finger tabs 60 located at the end of the housing element constricted inlet portion 36 and the injection port element 14 has a pair of curved recesses 62, only one of which is shown in FIG. 1, oppositely disposed with respect to one another on each side of the locking recess 54. The tabs and recesses facilitate the manual pressing together of the housing element 12 and injection port element 14, as well as the manual separation by pulling apart of the elements 12, 14 after use, subsequent to unlocking of the cap 24 from the locking recess 54. The cap 24 is connected to the housing element 12 at the top and side portion 18 adjacent the end 22 by a hinge element 64 which, in the preferred embodiment, is integrally molded with the cap 24 and hovel portion 16 of the same plastic material.

The invention claimed is:

1. A medical connector including:
   a male port element having a longitudinal passage extending therethrough and terminating at one end in sealing means which is of the self-sealing type;
   a housing element having a longitudinal cavity therein open at one end thereof, said housing member being adapted to have said port element inserted there within through said open mouth with the sealing means disposed in the cavity;
   a hollow needle fixed within said housing cavity and having a pointed tip at one end, said needle being disposed within the cavity so that the needle tip penetrates the sealing means upon insertion of the port element into the cavity; and
   means for detachably locking the housing element and the port element together when said port element is inserted into the cavity, said locking means including a locking cap element flexibly attached to the housing at the open end thereof and selectively operable to seal the housing open end if inserted thereinto and a locking recess formed on the port element and operable to receive the cap element when inserted thereinto to lock the port element and the housing element together in a mating relationship, said cap element being selectively manually removable from said housing open end and from said port element locking recess.

2. In a medical connector, the combination of:
   a housing having a generally cylindrical hollow barrel portion terminating at a first end in a constricted cylindrical inlet portion having an inlet remote from the barrel portion and having an outlet opening into the barrel portion, said inlet portion being adapted to receive a fluid inlet tube;
   hollow needle means disposed in said inlet portion outlet opening so as to close the opening to passage of fluid therethrough except through the needle, the needle having at least one needle point which is disposed within the barrel portion between the barrel portion first end and a second end of the barrel portion, opposite the first end, and which is normally open;
   barrel portion second end closure means comprising a cap means and means for flexibly attaching the cap to the barrel portion second end external of the opening therein so as to be selectively manually movable to seal the barrel second end to passage of fluid therethrough, said cap means having a first portion of a cross-sectionally size and configuration complementary to the barrel portion second end interior cross section so as to be operable to close the barrel second end to form said seal, said cap means having a second portion overlying said first portion and which extends beyond the periphery of the first portion and to which the flexible attaching means is connected, so that the flexible attaching means extends between the cap means second portion and the barrel adjacent the second end thereof;
   injection port means having a first portion which is generally frustoconical in configuration so as to taper to a blunt first end from a second portion of said injection port means generally axially aligned therewith, said second portion having a threaded annular external recess formed therein remote from the first portion and adapted to receive a fluid fitting, said injection port first and second portion having a passage extending longitudinally therethrough so as to permit the passage of fluid from an inlet portion of said longitudinal passage formed at said blunt end to an outlet portion of said longitudinal passage formed at said annular recess;
   said blunt end having a sealing element receiving recess formed thereon and adapted to receive a seal of the self-sealing type therein so as to seal the longitudinal passage against the flow of fluid therethrough;
   sealing means of the self-sealing type positioned over the blunt end and extending into the sealing recess; and
   locking means formed in said injection port for receiving said cap means when the injection port first end is inserted into the open hollow barrel housing second end in a mating relationship so that the needle point pierces the sealing means and extends into the longitudinal passage to selectively lock the housing means and the injection port means together.

3. A medical connector according to claim 2, and in which the locking means comprises a complementary recess formed on the port means and adapted to receive the cap first portion in a press-fit relationship when the housing means and injection port means are disposed in said mating relationship.

* * * * *